United States Patent
Kim

(10) Patent No.: US 12,251,473 B2
(45) Date of Patent: Mar. 18, 2025

(54) NON-SURFACTANT TYPE OIL-WATER DISPERSION COMPOSITION, NON-SURFACTANT TYPE WATER-OIL DISPERSION COMPOSITION, AND MANUFACTURING METHODS FOR BOTH COMPOSITIONS

(71) Applicants: SCAI Therapeutics Co., Ltd., Seoul (KR); Chul Hwan Kim, Daejeon (KR)

(72) Inventor: Chul Hwan Kim, Daejeon (KR)

(73) Assignees: SCAI THERAPEUTICS CO., LTD., Seoul (KR); Chul Hwan Kim, Daejeon (KR)

( * ) Notice: Subject to any disclaimer, the term of this patent is extended or adjusted under 35 U.S.C. 154(b) by 0 days.

(21) Appl. No.: 18/243,299

(22) Filed: Sep. 7, 2023

(65) Prior Publication Data

US 2023/0414513 A1     Dec. 28, 2023

Related U.S. Application Data

(62) Division of application No. 17/046,242, filed as application No. PCT/KR2019/004593 on Apr. 16, 2019, now Pat. No. 11,779,539.

(30) Foreign Application Priority Data

Apr. 17, 2018    (KR) ........................ 10-2018-0044547

(51) Int. Cl.
    *A61K 9/16*          (2006.01)
    *A61K 8/04*          (2006.01)
    (Continued)

(52) U.S. Cl.
    CPC .............. *A61K 9/1611* (2013.01); *A61K 8/04* (2013.01); *A61K 9/10* (2013.01); *A61K 31/196* (2013.01);
    (Continued)

(58) Field of Classification Search
    CPC ...... A61K 2800/33; A61K 8/04; A61K 8/375; A61K 2800/262; A61K 31/37;
    (Continued)

(56) References Cited

U.S. PATENT DOCUMENTS

| 5,968,549 A | 10/1999 | New et al. |
| 6,709,662 B1 * | 3/2004 | Gers-Barlag .......... A61Q 17/04 424/59 |

(Continued)

FOREIGN PATENT DOCUMENTS

| JP | 10-510256 A | 10/1998 |
| JP | 2000-095635 A | 4/2000 |

(Continued)

OTHER PUBLICATIONS

Younjin Min et al., "The role of interparticle and external forces in nanoparticle assembly", Macmillan Publishers Limited, vol. 7, pp. 527-538, Jul. 2008.

(Continued)

*Primary Examiner* — Jianfeng Song
(74) *Attorney, Agent, or Firm* — Sughrue Mion, PLLC

(57) ABSTRACT

A non-surfactant type oil-water (O/W) dispersion composition containing non-polar solvent droplets in a polar solvent, of which transparency is 90-100%, and a non-surfactant type water-oil (W/O) dispersion composition containing polar solvent droplets in a non-polar solvent, of which transparency is 90-100% are disclosed. Also disclosed are methods for manufacturing methods for both of the compositions.

2 Claims, 6 Drawing Sheets

(51) Int. Cl.

| | | |
|---|---|---|
| *A61K 9/10* | (2006.01) | |
| *A61K 31/196* | (2006.01) | |
| *A61K 31/337* | (2006.01) | |
| *A61K 31/352* | (2006.01) | |
| *A61K 31/37* | (2006.01) | |
| *A61K 31/415* | (2006.01) | |
| *A61K 31/496* | (2006.01) | |
| *A61K 31/5415* | (2006.01) | |
| *A61K 31/704* | (2006.01) | |
| *A61K 31/7068* | (2006.01) | |
| *A61K 38/13* | (2006.01) | |

(52) U.S. Cl.
 CPC .......... *A61K 31/337* (2013.01); *A61K 31/352* (2013.01); *A61K 31/37* (2013.01); *A61K 31/415* (2013.01); *A61K 31/496* (2013.01); *A61K 31/5415* (2013.01); *A61K 31/704* (2013.01); *A61K 31/7068* (2013.01); *A61K 38/13* (2013.01)

(58) Field of Classification Search
 CPC .. A61K 31/352; A61K 31/7068; A61K 38/13; A61K 31/496; A61K 9/1611; A61K 31/196; A61K 31/5415; A61K 31/704; A61K 2800/10; A61K 9/10; A61K 8/922; A61K 9/107; A61K 8/064; A61K 31/415; A61K 31/337; A61K 8/062; A61Q 19/00
 See application file for complete search history.

(56) References Cited

U.S. PATENT DOCUMENTS

| | | | |
|---|---|---|---|
| 8,181,941 | B2 | 5/2012 | Von Wimmersperg |
| 8,470,873 | B2 | 6/2013 | Chen |
| 2007/0207173 | A1 | 9/2007 | Chen |
| 2008/0262103 | A1 | 10/2008 | Stork et al. |
| 2010/0016200 | A1 | 1/2010 | Nagare et al. |
| 2010/0136207 | A1 | 6/2010 | Kim et al. |
| 2015/0196481 | A1 | 7/2015 | Mitra et al. |
| 2015/0231070 | A1 | 8/2015 | Huang |
| 2016/0199269 | A1 | 7/2016 | Lee |
| 2016/0271023 | A1 | 9/2016 | Bekemeier et al. |
| 2017/0112764 | A1 | 4/2017 | Wu |
| 2017/0319458 | A1 | 11/2017 | Matsufuji et al. |
| 2017/0360661 | A1 | 12/2017 | Cassin et al. |

FOREIGN PATENT DOCUMENTS

| | | |
|---|---|---|
| JP | 2006-281038 A | 10/2006 |
| JP | 2009-525342 A | 7/2009 |
| JP | 2015-124168 A | 7/2015 |
| JP | 2018-501242 A | 1/2018 |
| KR | 10-2004-0035320 A | 4/2004 |
| KR | 10-0452165 B1 | 10/2004 |
| KR | 10-0482355 B1 | 4/2005 |
| KR | 10-2005-0078683 A | 8/2005 |
| KR | 10-2006-0004918 A | 1/2006 |
| KR | 10-0823345 B1 | 4/2008 |
| KR | 10-0836035 B1 | 6/2008 |
| KR | 10-2008-0091286 A | 10/2008 |
| KR | 10-0878026 B1 | 1/2009 |
| KR | 10-2009-0051745 A | 5/2009 |
| KR | 10-0951706 B1 | 4/2010 |
| KR | 10-2010-0092594 A | 8/2010 |
| KR | 10-0991675 B1 | 11/2010 |
| KR | 10-1002433 B1 | 12/2010 |
| KR | 10-1015384 B1 | 2/2011 |
| KR | 10-1038589 B1 | 6/2011 |
| KR | 10-1043355 B1 | 6/2011 |
| KR | 10-2012-0042396 A | 5/2012 |
| KR | 10-1157144 B1 | 6/2012 |
| KR | 10-1192161 B1 | 10/2012 |
| KR | 10-1199966 B1 | 11/2012 |
| KR | 10-2013-0025988 A | 3/2013 |
| KR | 10-1259452 B1 | 4/2013 |
| KR | 10-1270300 B1 | 5/2013 |
| KR | 10-1315440 B1 | 10/2013 |
| KR | 10-1199580 B1 | 11/2013 |
| KR | 10-1332064 B1 | 11/2013 |
| KR | 10-1399706 B1 | 5/2014 |
| KR | 10-1472304 B1 | 12/2014 |
| KR | 10-1529480 B1 | 6/2015 |
| KR | 10-2015-0086284 A | 7/2015 |
| KR | 10-2016-0095089 A | 8/2016 |
| KR | 10-2016-0101913 A | 8/2016 |
| KR | 10-1654576 B1 | 9/2016 |
| KR | 10-1659653 B1 | 10/2016 |
| KR | 10-1674014 B1 | 11/2016 |
| KR | 10-2016-0146669 A | 12/2016 |
| KR | 10-2017-0002989 A | 1/2017 |
| KR | 10-2017-0048190 A | 5/2017 |
| KR | 10-2017-0094345 A | 8/2017 |
| KR | 10-2017-0097709 A | 8/2017 |
| KR | 10-2019-0121055 A | 10/2019 |
| WO | WO-2015099198 A1 * | 7/2015 ............. A61K 8/062 |

OTHER PUBLICATIONS

Hai Ming Lu et al., "Size-Dependent Surface Tension and Tolman's Length of Droplets", Langmuir 2005, 21, pp. 779-781.

Øivind Wilhelmsen et al., "Communication: Tolman length and rigidity constants of water and their role in nucleation", The Journal of Chemical Physics, vol. 142, pp. 171103-1-171103-5, 2015.

Mohammad Hassan Shahavi et al., "Evaluation of critical parameters for preparation of stable clove oil nanoemulsion", Arabian Journal of Chemistry, 2015, pp. 1-6.

Yeon-Ji Jo et al., "Preparation of Nanoemulsions Containing Curcumin by High Pressure Homogenization", vol. 18, No. 4. pp. 341-347, 2014.

In-Sang Yoo "Formation and Stability of Nanoemulsion Containing CoQ10 by Mechanical Emulsification", Appl. Chem. Eng., vol. 23, No. 5, Oct. 2012, pp. 467-473.

Myoung Sun Lim et al., "Preparation of Nano-emulsion Containing Polygonum aviculare Extract for Enhanced Transdermal Delivery", Appl. Chem. Eng., vol. 23, No. 2, Apr. 2012, pp. 222-227.

International Search Report issued Jul. 19, 2019 in International Application No. PCT/KR2019/004593.

Susanne Sihler et al., "Highly Transparent w/o Pickering Emulsions without Adjusting the Refractive Index of the Stabilizing Particles", Langmuir, 2017, vol. 33, No. 39, pp. 10302-10310 (9 pages total).

Koji Nakabayashi et al., "Highly clear and transparent nanoemulsion preparation under surfactant-free conditions using tandem acoustic emulsification", ChemComm, 2011, vol. 47, No. 20, pp. 5765-5767 (3 pages total).

* cited by examiner

[Figure 1]
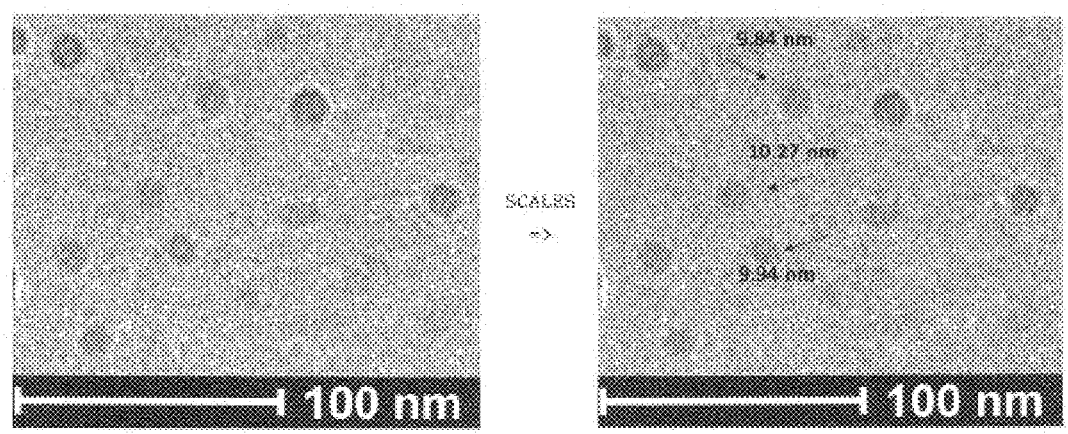
[Figure 2]
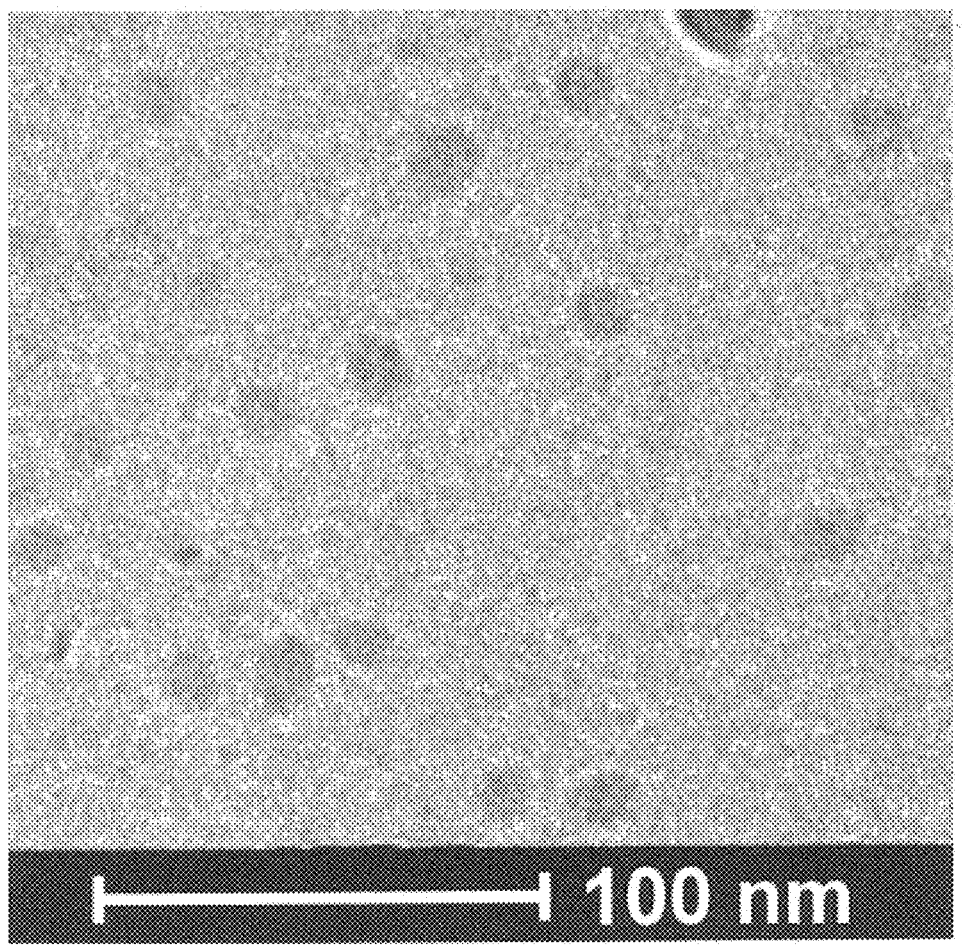

[Figure 3]
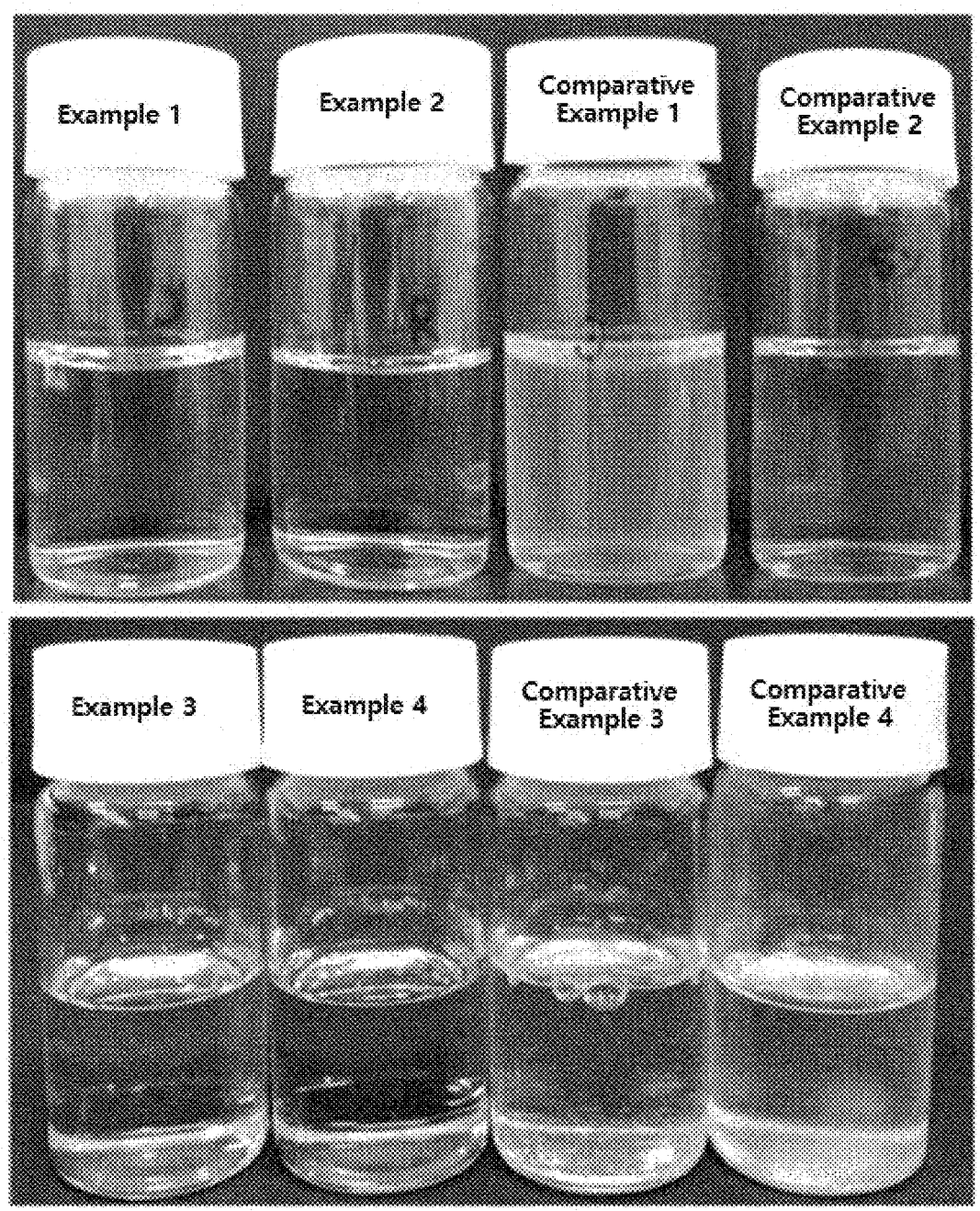

[Figure 4]
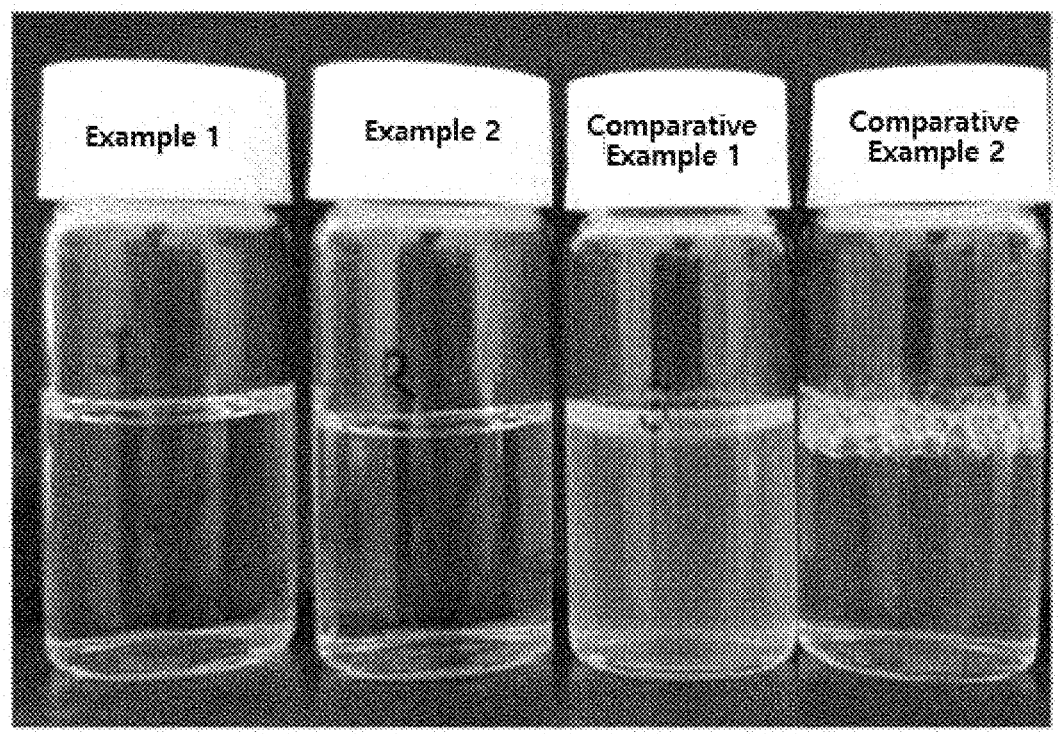
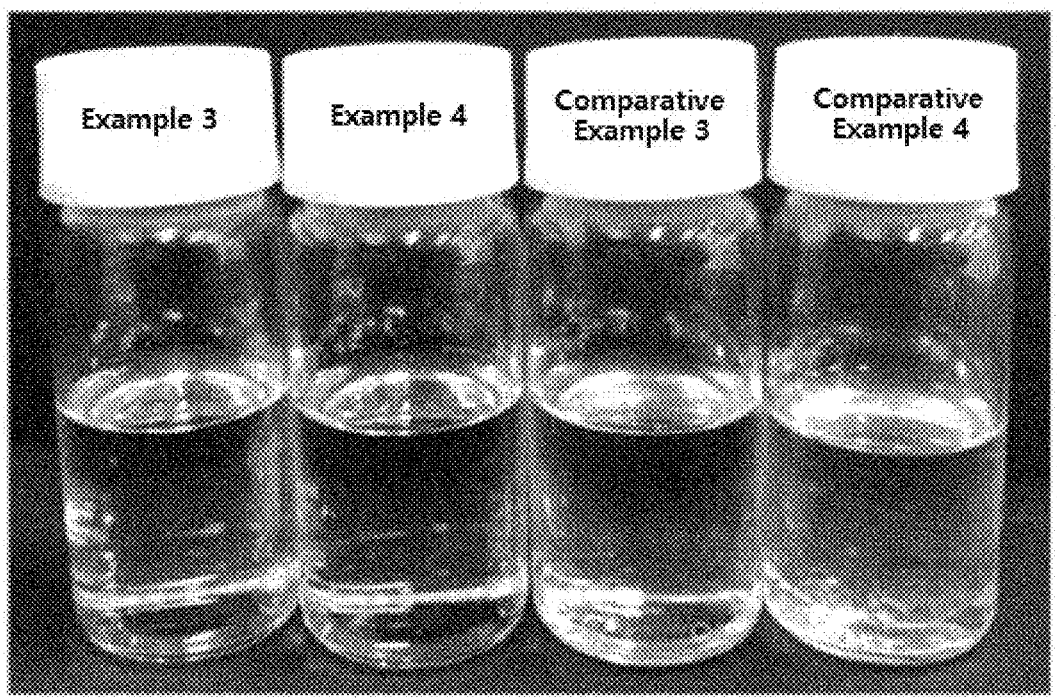

[Figure 5]
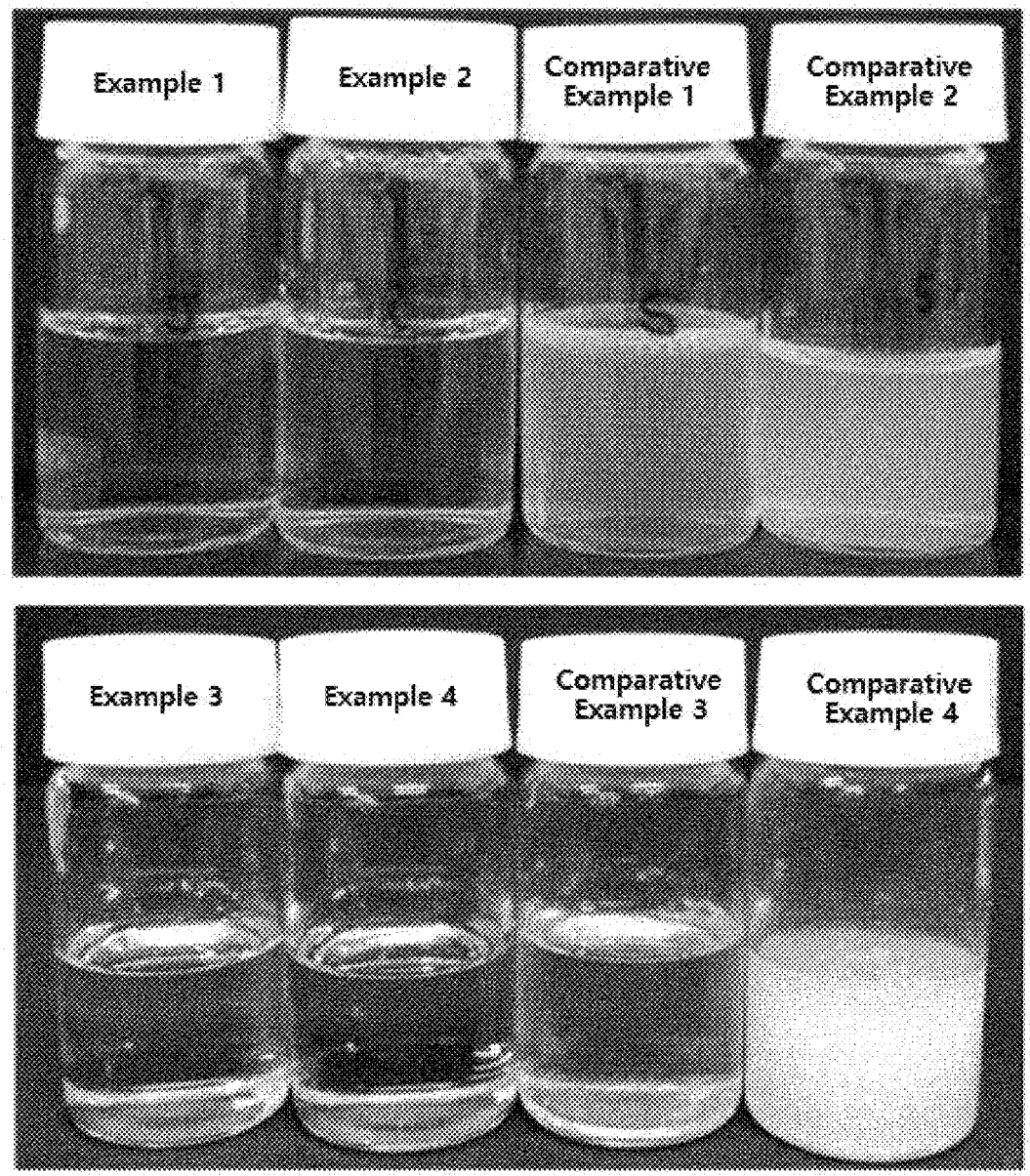

[Figure 6]
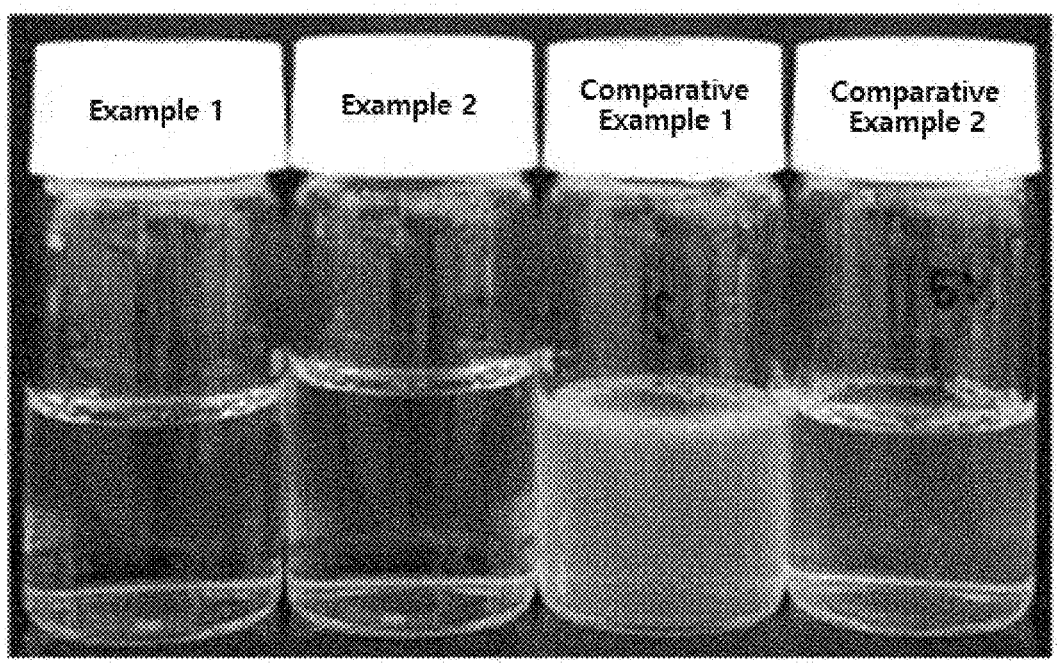
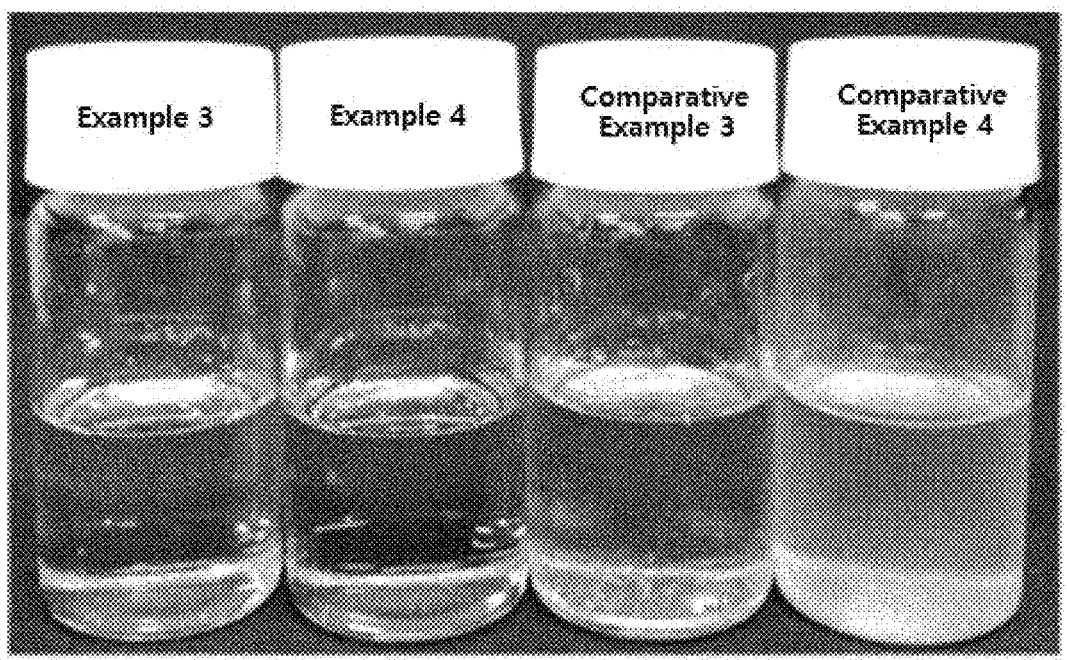

[Figure 7]
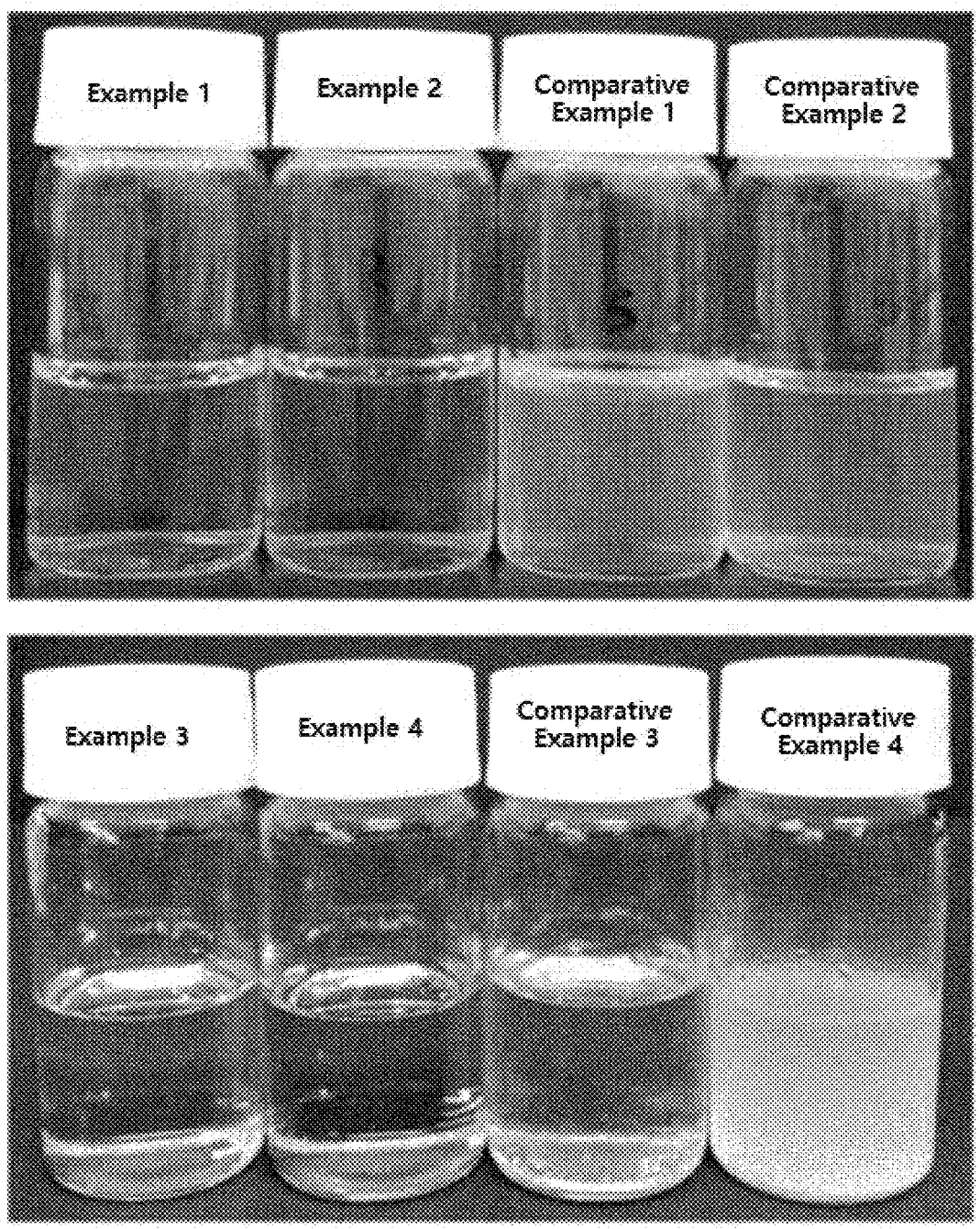

NON-SURFACTANT TYPE OIL-WATER DISPERSION COMPOSITION, NON-SURFACTANT TYPE WATER-OIL DISPERSION COMPOSITION, AND MANUFACTURING METHODS FOR BOTH COMPOSITIONS

CROSS-REFERENCE TO RELATED APPLICATIONS

This application is a Divisional application of U.S. patent application Ser. No. 17/046,242, filed Oct. 8, 2020 (allowed), which is a National Stage of International Application No. PCT/KR2019/004593 filed Apr. 16, 2019, which claims priority under U.S.C. § 119(a) to Korean Patent Application No. 10-2018-0044547 filed Apr. 17, 2018.

TECHNICAL FIELD

The present invention relates to a non-surfactant type oil-water (O/W) dispersion composition, a non-surfactant type water-oil (W/O) dispersion composition, and manufacturing methods for both of the compositions, more particularly, to a non-surfactant type oil-water (O/W) dispersion composition and a non-surfactant type water-oil (W/O) dispersion composition having excellent dispersion stability without including a surfactant, and manufacturing methods for both of the compositions.

BACKGROUND ART

Conventional droplets adhere to each other by physical and chemical attraction such as van der Waals force and surface tension. In order to pulverize and disperse droplets present in the solution, there must be a force greater than the aforementioned attraction force, and conventional dispersion methods such as the ball-mill method have a problem that impurities are included in the dispersion process. Therefore, various methods have been attempted to prevent aggregation between these droplets.

One of them is to use a surfactant. In particular, in the case of oil-in-water (O/W) dispersion in which oil is dispersed in water, or water-in-oil (W/O) dispersion in which water is dispersed in oil, sufficient stability can be maintained by using an additional surfactant required for emulsification in order to stabilize the dispersion state of the dispersion.

However, when a surfactant is used, there is an advantage of being able to stabilize through uniform dispersion, but there are serious disadvantages in terms of usability such as poor spreadability, stickiness that makes the feeling of use unpleasant, and a large amount of residual oil, due to the use of the surfactant, and also there was a problem that rash was caused in the user due to the use of the surfactant.

In addition, in the case of conventional dispersion, there was a problem that as ultrasonic waves are applied or it is used for a long time at high or low temperature, the degree of dispersion was lowered, causing a phase separation phenomenon between water and oil.

Therefore, there is a need for research on dispersion in which phase separation does not occur even when the environment changes, while it can stably disperse water and oil even without using the surfactant.

(Patent Document 1) Korean Laid-open Patent Publication No. 10-2011-0053775 (May 24, 2011), A Dispersing Apparatus for Nano Powders Using Intensity Focused Ultrasonics Wave and A Dispersing Method Using Thereof.

DISCLOSURE

Technical Problem

Accordingly, the inventors of the present invention have completed the present invention by confirming that if droplets having a very small size are manufactured, it is possible to secure excellent dispersibility even without using a surfactant.

Therefore, it is an object of the present invention to provide a non-surfactant type oil-water (O/W) dispersion composition or a non-surfactant type water-oil (W/O) dispersion composition having excellent transdermal delivery effect without causing a phase separation phenomenon even when a use environment is changed, while having good usability, such as good spreadability and applicability by not using a surfactant.

It is another object of the present invention to provide a cosmetic composition or pharmaceutical composition comprising the composition.

Technical Solution

In order to achieve the above objects, the present invention provides a non-surfactant type oil-water (O/W) dispersion composition comprising non-polar solvent droplets in a polar solvent, wherein the transparency of the dispersion composition is 90 to 100%.

In addition, the present invention provides a manufacturing method of non-surfactant type oil-water (O/W) dispersion composition, comprising the steps of a) impregnating silica with a non-polar solvent; b) mixing the silica impregnated with the non-polar solvent prepared in step a) with a polar solvent; and c) incorporating non-polar solvent droplets into the polar solvent by applying an impact to the silica impregnated with the non-polar solvent prepared in step b) to generate the non-polar solvent droplets.

The present invention provides a non-surfactant type water-oil (W/O) dispersion composition comprising polar solvent droplets in a non-polar solvent, wherein the transparency of the dispersion composition is 90 to 100%.

In addition, the present invention provides a manufacturing method of the non-surfactant type water-oil (W/O) dispersion composition of claim 1, comprising the steps of a) impregnating silica with a polar solvent; b) mixing the silica impregnated with the polar solvent prepared in step a) with a non-polar solvent; and c) incorporating polar solvent droplets into the non-polar solvent by applying energy to the mixture of the silica impregnated with the polar solvent and the non-polar solvent prepared in step b) to generate polar solvent droplets.

Advantageous Effects

The dispersion composition of the present invention not only has the advantage of not causing a phase separation phenomenon even when the use environment is changed, but also has the advantage of good usability such as good spreadability and applicability, when used on the skin, by not using a surfactant.

In addition, there is an advantage that a poorly soluble material or a poorly dispersible material can be easily incorporated.

In addition, since various active ingredients can be added into droplets with a very small size, when an ingredient with a pharmacological effect is added, transdermal delivery function through the skin is improved and the absorption rate is excellent, and thus it can also be used in various medical products.

In addition, ingredients with pharmacological effects can be delivered through oral administration and intravenous injection, and thus can be also used in such pharmaceutical products.

Due to these advantages, it can be used in various cosmetic compositions and pharmaceutical compositions.

DESCRIPTION OF DRAWINGS

FIG. 1 are photographs of droplets in an oil-water (O/W) dispersion composition according to an embodiment of the present invention, which was taken using a CryoTEM (JEOL company, JEM-3011HR, FEI company, Tecnai G2 spirit TWIN) device.

FIG. 2 is another photograph of droplets in an oil-water (O/W) dispersion composition according to an embodiment of the present invention.

FIGS. 3 and 4 are photographs showing phase separation characteristics of an oil-water (O/W) dispersion composition according to an embodiment of the present invention.

FIGS. 5 to 7 are photographs showing temperature stability characteristics of an oil-water (O/W) dispersion composition according to an embodiment of the present invention.

BEST MODE

In the present invention, a dispersion composition comprising a polar solvent and a non-polar solvent is proposed, which not only has good usability such as good spreadability and applicability, when used on the skin, by not comprising a surfactant, but also does not cause a phase separation phenomenon even when the use environment is changed, and which makes it possible to add various active ingredients into droplets having a very small size, when adding ingredients with pharmacological effect, and thus has excellent transdermal delivery function through skin, etc. and also has excellent absorption due to its improved performance for intravenous injection or oral administration.

It will be described in more detail below.

Non-Surfactant Type Oil-Water (O/W) Dispersion Composition

The non-surfactant type oil-water (O/W) dispersion composition referred to in the present specification is a dispersion composition comprising non-polar solvent droplets in a polar solvent, wherein the dispersion composition has a transparency of 90 to 100%. In the case of general oil-water dispersion composition, it comprises a surfactant to prevent phase separation phenomenon and facilitate dispersion. However, when a surfactant is used, there is an advantage of being able to stabilize through uniform dispersion, but there are serious disadvantages in terms of usability such as poor spreadability, stickiness that makes the feeling of use unpleasant, and a large amount of residual oil, due to the use of the surfactant.

Therefore, the inventors of the present invention have completed the present invention by confirming that when non-polar solvent droplets having a very small size are manufactured, excellent dispersibility can be secured even if a surfactant is not used, thus improving transparency of dispersion composition.

In the present invention, the transparency refers to the degree of clearness of a material, which is obtained by dividing the amount of light transmitted through the medium by the amount of incident light. Therefore, more transparent material indicates a value close to 100%, and more opaque material indicates a value close to 0%. In the present invention, the transparency at UV 650 nm was measured and shown.

The non-surfactant type oil-water (O/W) dispersion composition of the present invention comprises a polar solvent.

The polar solvent used in the present invention may be used without particular limitation as long as it is a solvent that can be mixed with water in a conventional sense. Specifically, water, an alcohol having 1 to 10 carbon atoms, acetone, and the like may be used.

The non-surfactant type oil-water (O/W) dispersion composition of the present invention comprises a non-polar solvent.

The droplets of the non-polar solvent used in the present invention refer to a state in which the non-polar solvent is dispersed in the polar solvent in a spherical or non-spherical form. The type of the non-polar solvent used in the present invention is not particularly limited as long as it is a material that can be mixed with oil, and preferably, the non-polar solvent may be at least one selected from the group consisting of oil, hexane, chloroform, dichloromethane, ethyl acetate, and the like, and preferably oil.

The droplets of the non-polar solvent used in the present invention have a spherical or non-spherical shape. In the present invention, the spherical shape is a concept including a polyhedron close to a perfect sphere as well as a perfectly smooth sphere, which is assumed to have a non-spherical shape, assuming that substantially perfect spherical droplets do not exist.

Accordingly, the droplets of the non-polar solvent used in the present invention comprise droplets having a sphericity of 0.7 to 1. Here, the "sphericity" is defined as r/R, wherein R is the diameter of the circle equal to the projected area of the droplet, and r is the diameter of the smallest circle circumscribed to the projected image of the droplet. The closer the value of the sphericity is to 1, the more complete the shape of the sphere is, and the closer it is to 0, the more it deviates from the shape of the sphere. It is preferable that the droplets used in the present invention have a sphericity of 0.7 to 1. The droplets used in the present invention may comprise droplets having an ellipsoid or a polyhedral shape having some protruding portions and may comprise other types of droplets and any possible form without limitation thereto.

Among the droplets of the non-polar solvent used in the present invention, droplets that are non-spherical may be expressed in an elliptical shape. Accordingly, the droplets of the non-polar solvent used in the present invention may comprise elliptical droplets having an average ratio of long diameter/short diameter of 1 to 1000, more preferably 5 to 100.

In the present invention, the sphericity of the droplets of the non-polar solvent and the ratio of the long diameter/short diameter thereof are values measured using a photograph of the non-surfactant type oil-water (O/W) dispersion composition comprising the droplets of the non-polar solvent, taken at a magnification (10,000 to 50,000 times) that can be measured using an electron microscope (e.g. TEM). The long diameter is the length of the long side of the rectangle drawn so that it is in contact with the droplet's outer edge and also has its smallest area, and the short diameter is the length of the short side of the rectangle. The average of the long and short diameters is an average of 50 or more droplets randomly selected from the measurable droplets on the SEM image. The droplet that can be measured on an SEM photograph refers to a droplet with a short diameter of 0.01 µm or more, for example, in the case of an SEM photograph having a magnification of 10,000 times.

The non-polar solvent droplets comprised in the non-surfactant type oil-water (O/W) dispersion composition of the present invention may have an average particle diameter of 20 nm or less, preferably 15 nm or less, most preferably, nm or less. The average particle diameter may be measured through a diffraction experiment, and preferably may be measured using Small Angle Neutron Scattering (SANS). If the average particle diameter of the droplets of the non-polar solvent exceeds 20 nm, there is a problem that the dispersibility is deteriorated and a phase separation phenomenon occurs. In addition, the lower limit of the average particle diameter of the droplets of the non-polar solvent is not particularly limited, but may be about 1 nm or more.

In the non-polar solvent droplets comprised in the non-surfactant type oil-water (O/W) dispersion composition of the present invention, the particle diameter of the long diameter of the droplets has a span $\Delta D$ in the range of 0.2 to 3, and the span $\Delta D$ can be calculated according to Equation 1 below.

$$\Delta D = (D_{90} - D_{10})/D_{50} \quad \text{[Equation 1]}$$

If the span $\Delta D$ is less than 0.2, there is a problem that it is difficult to manufacture these droplets. If the span $\Delta D$ is greater than 3, there is a problem that the dispersibility is deteriorated and a phase separation phenomenon occurs.

According to the manufacturing method of the non-surfactant type oil-water (O/W) dispersion composition of the present invention, the proportion of droplets with the particle diameter of the long diameter of 20 nm or less in the non-polar solvent droplets comprised in the composition is 50% or more. If the ratio of droplets with the particle diameter of the long diameter of the non-polar solvent droplets of less than 20 nm is less than 50%, there is a problem that the dispersibility is deteriorated and a phase separation phenomenon occurs.

Between the dispersed droplets, physical and chemical attraction such as van der Waals force and surface tension are generated, resulting in a phenomenon of clumping together. To control this phenomenon, $\Delta H$ of the Gibbs energy acting between droplets must be adjusted.

However, when droplets having nano-size such as the non-polar solvent droplets comprised in the non-surfactant type oil-water (O/W) dispersion composition of the present invention are in their lowest thermodynamic energy state, they do not self-assemble unless there is an external input of energy or force (see "The role of interparticle and external forces in nanoparticle assembly", Nature Materials 7, 527-538 (2008)).

With this in mind, the inventors of the present invention take advantage of the fact that $\Delta H$ of Gibbs energy can be adjusted by reducing the size of the dispersed droplets to the nanoscale and thus have strengthened the dispersion power so that the droplets do not clump together and are well dispersed, and there is no phase separation even in external energy such as ultrasonic waves or cryogenic or extremely high temperatures.

In addition, the non-polar solvent droplets comprised in the non-surfactant type oil-water (O/W) dispersion composition of the present invention may be comprised in an amount of 0.01 wt. % (W/W) to 30 wt. % (W/W), preferably 0.1 wt. % (W/W) to 15 wt. % (W/W), based on the total weight of the composition.

If the weight of the non-polar solvent droplets is less than 0.01 wt. % (W/W), there is a problem that the content of the active ingredient is too small. If the weight of the non-polar solvent droplets is more than 30.0 wt. % (W/W), there is a problem that a phase inversion occurs in volume.

Further, an additive may be further comprised in the non-surfactant type oil-water (O/W) dispersion composition of the present invention.

The additive may be used without particular limitation as long as it is generally comprised in the aqueous solution, and preferably, a pH adjusting agent, an isotonic solution, an osmotic pressure stabilizer, an excipient, or a mixture thereof may be used.

In addition, the non-polar solvent droplets comprised in the non-surfactant type oil-water (O/W) dispersion composition of the present invention may further contain an active ingredient. The active ingredient may be used without particular limitation as long as it is a pharmaceutically useful substance or a substance having a medical effect, and as an example, cyclosporin A, paclitaxel, docetaxel, decursin, meloxicam, itraconazole, celecoxib, capecitabine, travo, frost, isoflavone, diclofenac sodium, ginsenoside Rg1, tacrolimus, alendronate, latanoprost, bimatoprost, atorvastatin calcium, rosuvastatin calcium, entecavir, amphotericin B, omega 3, ursodeoxycholic acid; fragrance oils such as eucalyptus oil, lavender oil, lemon oil, sandalwood oil, rosemary oil, chamomile oil, cinnamon oil, and orange oil; alphabisabolol, vitamin A (retinol), vitamin E, tocopheryl acetate, vitamin D, vitamin F, or derivatives thereof; or the like, or a combination thereof may be used.

In addition, the active ingredient may be comprised in an amount of 0.001 wt. % (W/W) to 20 wt. % (W/W) relative to non-polar solvent droplets.

Since the non-surfactant type oil-water (O/W) dispersion composition of the present invention comprises the active ingredient as described above, it can be used as a cosmetic composition or a pharmaceutical composition.

Since the non-surfactant type oil-water (O/W) dispersion composition of the present invention does not contain a surfactant, as mentioned above, it does not ionic bond with anions existing on the skin, and also since the size of the non-polar solvent droplets is 20 nm or less and is significantly smaller than the pores outside the skin (200 nm or more), it is easy to penetrate into the skin.

Therefore, when used as the cosmetic composition or pharmaceutical composition as described above, it is possible to deliver significantly faster and many active ingredients compared to the conventional composition.

Manufacturing Method of Non-Surfactant Type Oil-Water (O/W) Dispersion Composition In addition, the present invention provides a manufacturing method of non-surfactant type oil-water (O/W) dispersion composition, comprising the steps of a) impregnating silica with a non-polar solvent; b) mixing the silica impregnated with the non-polar solvent prepared in step a) with a polar solvent; and c) incorporating non-polar solvent droplets into the polar solvent by applying an impact to the silica impregnated with the non-polar solvent prepared in step b) to generate the non-polar solvent droplets.

The manufacturing method of the non-surfactant type oil-water (O/W) dispersion composition according to the present invention will be described for each step as follows. Step a) of the present invention is a step of impregnating silica with a non-polar solvent.

The non-polar solvent used in step a) is not particularly limited as long as it is a solvent that can be mixed with oil, and preferably the non-polar solvent may be at least one selected from the group consisting of oil, hexane, chloroform, dichloromethane, ethyl acetate, and the like, and preferably oil.

In addition, in step a), an active ingredient may be further added to the non-polar solvent. The active ingredient may be used without particular limitation as long as it is a pharmaceutically useful substance or a substance having a medical effect, and as an example, cyclosporin A, paclitaxel, docetaxel, decursin, meloxicam, itraconazole, celecoxib, capecitabine, travo, frost, isoflavone, diclofenac sodium, ginsenoside Rg1, tacrolimus, alendronate, latanoprost, bimatoprost, atorvastatin calcium, rosuvastatin calcium, entecavir, amphotericin B, omega 3, ursodeoxycholic acid; fragrance oils such as eucalyptus oil, lavender oil, lemon oil, sandalwood oil, rosemary oil, chamomile oil, cinnamon oil, and orange oil; alphabisabolol, vitamin A (retinol), vitamin E, tocopheryl acetate, vitamin D, vitamin F, or derivatives thereof; or the like, or a combination thereof may be used.

The silica can be used without any particular limitation as long as it has a nano-scale pore size and can impregnate a non-polar solvent. Preferably, silica having a pore size of 5 to 40 nm based on the diameter may be used. In this case, there is an advantage that it is easy to control the size of the non-polar solvent droplets to be described later.

Step b) of the present invention is a step of mixing the silica impregnated with the non-polar solvent prepared in step a) with a polar solvent.

In step b), the silica impregnated with the non-polar solvent prepared in step a) is filtered and mixed with a polar solvent.

The polar solvent used in the present invention may be used without particular limitation as long as it is a solvent that can be mixed with water in a conventional sense. Specifically, water, an alcohol having 1 to 10 carbon atoms, acetone, and the like may be used.

The amount of the polar solvent comprised in this case may be added so that the content of the non-polar solvent droplets is 0.01 wt. % (W/W) to 30 wt. % (W/W), and preferably the content of the non-polar solvent droplets is 0.1 wt. % (W/W) to 15 wt. % (W/W), when compared to the total weight of the composition of the non-polar solvent droplets impregnated in the silica and the polar solvent.

If the weight of the non-polar solvent droplets is less than 0.01 wt. % (W/W), there is a problem that the content of active ingredients is too small. If the weight of the non-polar solvent droplets is more than 30.0 wt. % (W/W), there is a problem that a phase inversion occurs in volume.

Step c) of the present invention is a step of incorporating non-polar solvent droplets into the polar solvent by applying an impact to the silica impregnated with the non-polar solvent prepared in step b) to generate non-polar solvent droplets.

According to the manufacturing method of the non-surfactant type oil-water (O/W) dispersion composition of the present invention, the non-polar solvent droplets with a size smaller than the pore size of silica can be obtained by impregnating oil into the pores of silica, and then applying ultrasonic waves, shear stress force or the like to the silica to remove the non-polar solvent impregnated in the pores of silica and make it into droplets. In the present invention, the size of the non-polar solvent droplets can be adjusted to the nanoscale level in the same manner as described above.

In the manufacturing method of the non-surfactant type oil-water (O/W) dispersion composition of the present invention, the method of applying ultrasonic waves to the silica is not particularly limited as long as it is capable of removing the non-polar solvent impregnated with the silica, but the dispersion device disclosed in Korean Patent Registration No. 10-1157144 may be preferably used.

In addition, in the manufacturing method of the non-surfactant type oil-water (O/W) dispersion composition, the method of applying a shear stress force to the silica may also be used without particular limitation as long as it is a method used in the art.

According to the manufacturing method of the non-surfactant type oil-water (O/W) dispersion composition of the present invention, the particle diameter of the long diameter of the droplets has a span ΔD in the range of 0.2 to 3, and the span ΔD can be calculated according to Equation 1 below.

$$\Delta D = (D_{90} - D_{10})/D_{50} \quad \text{[Equation 1]}$$

If the span ΔD is less than 0.2, there is a problem that it is difficult to manufacture these droplets. If the span ΔD is greater than 3, there is a problem that the dispersibility is deteriorated and a phase separation phenomenon occurs.

In addition, according to the manufacturing method of the non-surfactant type oil-water (O/W) dispersion composition of the present invention, the proportion of droplets with the particle diameter of the long diameter of nm or less in the non-polar solvent droplets comprised in the span composition in the range of 0.2 to 3 is 50% or more. If the ratio of droplets with the particle diameter of the long diameter of the non-polar solvent droplets of less than nm is less than 50%, there is a problem that the dispersibility is deteriorated and a phase separation phenomenon occurs.

Non-Surfactant Type Water-Oil (W/O) Dispersion Composition

The non-surfactant type water-oil (W/O) dispersion composition referred to in this specification is a dispersion composition comprising polar solvent droplets in a non-polar solvent, wherein the transparency of the dispersion composition is 90 to 100%. In the case of general water-oil dispersion composition, it comprises a surfactant to prevent phase separation phenomenon and facilitate dispersion. However, when a surfactant is used, there is an advantage of being able to stabilize through uniform dispersion, but there are serious disadvantages in terms of usability such as poor spreadability, stickiness that makes the feeling of use unpleasant, and a large amount of residual oil, due to the use of the surfactant.

Therefore, the inventors of the present invention have completed the present invention by confirming that when polar solvent droplets having a very small size are manufactured, excellent dispersibility can be secured even if a surfactant is not used, thus improving transparency of dispersion composition.

The non-surfactant type water-oil (W/O) dispersion composition of the present invention comprises a non-polar solvent.

The type of the non-polar solvent used in the present invention is not particularly limited as long as it is a material that can be mixed with oil, and preferably, the non-polar solvent may be at least one selected from the group consisting of oil, hexane, chloroform, dichloromethane, ethyl acetate, and the like, and preferably oil.

The non-surfactant type water-oil (W/O) dispersion composition of the present invention comprises a non-polar solvent.

The droplets of the polar solvent used in the present invention refer to a state in which the polar solvent is dispersed in the non-polar solvent in a spherical or non-spherical form.

The polar solvent used in the present invention may be used without particular limitation as long as it is a solvent that can be mixed with water in a conventional sense. Specifically, water, an alcohol having 1 to 10 carbon atoms, acetone, and the like may be used.

The droplets of the polar solvent used in the present invention have a spherical or non-spherical shape. In the present invention, the spherical shape is a concept including a polyhedron close to a perfect sphere as well as a perfectly smooth sphere, which is assumed to have a non-spherical shape, assuming that substantially perfect spherical droplets do not exist.

Accordingly, the droplets of the polar solvent used in the present invention comprise droplets having a sphericity of 0.7 to 1. Here, the "sphericity" is defined as r/R, wherein R is the diameter of the circle equal to the projected area of the droplet, and r is the diameter of the smallest circle circumscribed to the projected image of the droplet. The closer the value of the sphericity is to 1, the more complete the shape of the sphere is, and the closer it is to 0, the more it deviates from the shape of the sphere. It is preferable that the droplets used in the present invention have a sphericity of 0.7 to 1. The droplets used in the present invention may comprise droplets having an ellipsoid or a polyhedral shape having some protruding portions and may comprise other types of droplets and any possible form without limitation thereto.

Among the droplets of the polar solvent used in the present invention, droplets that are non-spherical may be expressed in an elliptical shape. Accordingly, the droplets of the polar solvent used in the present invention may comprise elliptical droplets having an average ratio of long diameter/short diameter of 1 to 1000, more preferably 5 to 100.

In the present invention, the sphericity of the droplets of the polar solvent and the ratio of the long diameter/short diameter thereof are values measured using a photograph of the non-surfactant type water-oil (W/O) dispersion composition comprising the droplets of the polar solvent, taken at a magnification (10,000 to 50,000 times) that can be measured using an electron microscope (e.g. TEM).

The long diameter is the length of the long side of the rectangle drawn so that it is in contact with the droplet's outer edge and also has its smallest area, and the short diameter is the length of the short side of the rectangle. In addition, the average of the long and short diameters is an average of 50 or more droplets randomly selected from the measurable droplets on the SEM image. The droplet that can be measured on an SEM photograph refers to a droplet with a short diameter of 0.01 μm or more, for example, in the case of an SEM photograph having a magnification of 10,000 times.

The polar solvent droplets comprised in the non-surfactant type water-oil (O/W) dispersion composition of the present invention may have an average particle diameter of 20 nm or less, preferably 15 nm or less, most preferably, 10 nm or less. The average particle diameter may be measured through a diffraction experiment, and preferably may be measured using Small Angle Neutron Scattering (SANS). If the average particle diameter of the droplets of the polar solvent exceeds 20 nm, there is a problem that the dispersibility is deteriorated and a phase separation phenomenon occurs. In addition, the lower limit of the average particle diameter of the droplets of the polar solvent is not particularly limited, but may be about 1 nm or more.

In the polar solvent droplets comprised in the non-surfactant type water-oil (W/O) dispersion composition of the present invention, the particle diameter of the long diameter of the droplets has a span ΔD in the range of 0.2 to 3, and the span ΔD can be calculated according to Equation 1 below.

$$\Delta D = (D_{90} - D_{10})/D_{50} \quad \text{[Equation 1]}$$

If the span ΔD is less than 0.2, there is a problem that it is difficult to manufacture these droplets. If the span ΔD is greater than 3, there is a problem that the dispersibility is deteriorated and a phase separation phenomenon occurs.

In addition, the proportion of droplets with the particle diameter of the long diameter of 20 nm or less in the polar solvent droplets comprised in the non-surfactant type water-oil (W/O) dispersion composition of the present invention is 50% or more. If the ratio of droplets with the particle diameter of the long diameter of the polar solvent droplets of less than 20 nm is less than 50%, there is a problem that the dispersibility is deteriorated and a phase separation phenomenon occurs.

Between the dispersed droplets, physical and chemical attraction such as van der Waals force and surface tension are generated, resulting in a phenomenon of clumping together. To control this phenomenon, ΔH of the Gibbs energy acting between droplets must be adjusted.

However, when droplets having nano-size such as the non-polar solvent droplets comprised in the non-surfactant type oil-water (O/W) dispersion composition of the present invention are in their lowest thermodynamic energy state, they do not self-assemble unless there is an external input of energy or force (see "The role of interparticle and external forces in nanoparticle assembly", Nature Materials 7, 527-538 (2008)).

With this in mind, the inventors of the present invention take advantage of the fact that ΔH of Gibbs energy can be adjusted by reducing the size of the dispersed droplets to the nanoscale and thus have strengthened the dispersion power so that the droplets do not clump together and are well dispersed, and there is no phase separation even in external energy such as ultrasonic waves or cryogenic or extremely high temperatures.

In addition, the polar solvent droplets comprised in the non-surfactant type water-oil (W/O) dispersion composition of the present invention may be comprised in an amount of 0.01 wt. % (W/W) to 30 wt. % (W/W), preferably 0.1 wt. % (W/W) to 15 wt. % (W/W), based on the total weight of the composition.

If the weight of the non-polar solvent droplets is less than 0.01 wt. % (W/W), there is a problem that the content of the active ingredient is too small. If the weight of the non-polar solvent droplets is more than 30.0 wt. % (W/W), there is a problem that a phase inversion occurs in volume.

Further, an additive may be further comprised in the non-surfactant type water-oil (W/O) dispersion composition of the present invention.

The additive may be used without particular limitation as long as it is generally comprised in the aqueous solution, and preferably, a pH adjusting agent, an isotonic solution, an osmotic pressure stabilizer, an excipient, or a mixture thereof may be used.

In addition, the polar solvent droplets comprised in the non-surfactant type water-oil (W/O) dispersion composition of the present invention may further contain an active ingredient. The active ingredient may be used without particular limitation as long as it is a pharmaceutically useful substance or a substance having a medical effect, and as an example, adenosine, arbutin, vitamin C, and hydrophilic derivatives thereof; vitamin B3, vitamin B5, vitamin H, and derivatives thereof; acetylglucosamine; and peptide; or the like, or a combination thereof may be used.

In addition, the active ingredient may be comprised in an amount of 0.001 wt. % (W/W) to 20 wt. % (W/W) relative to the polar solvent droplets.

Since the non-surfactant type water-oil (W/O) dispersion composition of the present invention comprises the active ingredient as described above, it can be used as a cosmetic composition or a pharmaceutical composition.

Since the non-surfactant type water-oil (W/O) dispersion composition of the present invention does not contain a surfactant, as mentioned above, it does not ionic bond with anions existing on the skin, and also since the size of the non-polar solvent droplets is 20 nm or less and is significantly smaller than the pores outside the skin (200 nm or more), it is easy to penetrate into the skin.

Therefore, when used as the cosmetic composition or pharmaceutical composition as described above, it is possible to deliver significantly faster and many active ingredients compared to the conventional composition.

Manufacturing Method of Non-Surfactant Type Water-Oil (W/O) Dispersion Composition In addition, the present invention provides a manufacturing method of the non-surfactant type water-oil (W/O) dispersion composition, comprising the steps of a) impregnating silica with a polar solvent; b) mixing the silica impregnated with the polar solvent prepared in step a) with a non-polar solvent; and c) incorporating polar solvent droplets into the non-polar solvent by applying energy to the mixture of the silica impregnated with the polar solvent and the non-polar solvent prepared in step b) to generate polar solvent droplets.

The manufacturing method of the non-surfactant type water-oil (W/O) dispersion composition according to the present invention will be described for each step as follows.

Step a) of the present invention is a step of impregnating silica with a polar solvent.

The polar solvent used in step a) is not particularly limited as long as it is a solvent that can be mixed with oil, and preferably the polar solvent may be at least one selected from the group consisting of oil, hexane, chloroform, dichloromethane, ethyl acetate, and the like, and preferably oil.

In addition, in step a), an active ingredient may be further added to the polar solvent. The active ingredient may be used without particular limitation as long as it is a pharmaceutically useful substance or a substance having a medical effect, and as an example, adenosine, arbutin, vitamin C, and hydrophilic derivatives thereof; vitamin B3, vitamin B5, vitamin H, and derivatives thereof; acetylglucosamine; and peptide; or the like, or a combination thereof may be used.

The silica can be used without any particular limitation as long as it has a nano-scale pore size and can impregnate a polar solvent. Preferably, silica having a pore size of 5 to 40 nm based on the diameter may be used. In this case, there is an advantage that it is easy to control the size of the polar solvent droplets to be described later.

Step b) of the present invention is a step of mixing the silica impregnated with the polar solvent prepared in step a) with a non-polar solvent.

In step b), the silica impregnated with the polar solvent prepared in step a) is filtered and mixed with a non-polar solvent.

The non-polar solvent used in the present invention may be used without particular limitation as long as it is a solvent that can be mixed with water in a conventional sense. Specifically, water, an alcohol having 1 to 10 carbon atoms, acetone, and the like may be used.

The amount of the non-polar solvent comprised in this case may be added so that the content of the polar solvent droplets is 0.01 wt. % (W/W) to 30 wt. % (W/W), and preferably the content of the polar solvent droplets is 0.1 wt. % (W/W) to 15 wt. % (W/W), when compared to the total weight of the composition of the polar solvent droplets impregnated in the silica and the non-polar solvent.

If the weight of the polar solvent droplets is less than 0.01 wt. % (W/W), there is a problem that the content of active ingredients is too small. If the weight of the polar solvent droplets is more than 30.0 wt. % (W/W), there is a problem that a phase inversion occurs in volume.

Step c) of the present invention is a step of incorporating polar solvent droplets into the non-polar solvent by applying an impact to the silica impregnated with the polar solvent prepared in step b) to generate polar solvent droplets.

According to the manufacturing method of the non-surfactant type water-oil (W/O) dispersion composition of the present invention, the polar solvent droplets with a size smaller than the pore size of silica can be obtained by impregnating oil into the pores of silica, and then applying ultrasonic waves, shear stress force or the like to the silica to remove the polar solvent impregnated in the pores of silica and make it into droplets. In the present invention, the size of the polar solvent droplets can be adjusted to the nanoscale level in the same manner as described above.

In the manufacturing method of the non-surfactant type water-oil (W/O) dispersion composition of the present invention, the method of applying ultrasonic waves to the silica is not particularly limited as long as it is capable of removing the polar solvent impregnated with the silica, but the dispersion device disclosed in Korean Patent Registration No. 10-1157144 may be preferably used.

In addition, in the manufacturing method of the non-surfactant type water-oil (W/O) dispersion composition, the method of applying a shear stress force to the silica may also be used without particular limitation as long as it is a method used in the art.

According to the manufacturing method of the non-surfactant type water-oil (W/O) dispersion composition of the present invention, the particle diameter of the long diameter of the polar solvent droplets comprised in the non-surfactant type water-oil (W/O) dispersion composition of the present invention has a span $\Delta D$ in the range of 0.2 to 3, and the span $\Delta D$ can be calculated according to Equation 1 below.

$$\Delta D = (D_{90} - D_{10})/D_{50} \qquad \text{[Equation 1]}$$

If the span $\Delta D$ is less than 0.2, there is a problem that it is difficult to manufacture these droplets. If the span $\Delta D$ is greater than 3, there is a problem that the dispersibility is deteriorated and a phase separation phenomenon occurs.

In addition, according to the manufacturing method of the non-surfactant type water-oil (W/O) dispersion composition of the present invention, the proportion of droplets with the particle diameter of the long diameter of 20 nm or less in the polar solvent droplets comprised in the composition in the range of 0.2 to 3 is 50% or more. If the ratio of droplets with the particle diameter of the long diameter of the polar solvent droplets of less than 20 nm is less than 50%, there is a problem that the dispersibility is deteriorated and a phase separation phenomenon occurs.

Hereinafter, the present invention will be described in more detail the manufacturing method of the present invention through examples of the present invention. It is obvious that the present invention is not limited to these examples.

EXAMPLES

Manufacture of Non-Surfactant Type Oil-Water (O/W) Dispersion Composition

Example 1 of aerogel (JIOS company, product name AeroVa) having a pore size of 20 nm or less is heat-treated at 450° C. for 2 hours using a furnace (Furnace, JSR company, JSMF-45T). After adding 8 g of fragrance oil to 4 g of heat-treated aerogel, an overhead stirrer (M TOPS® company, BL620D) is used to impregnate the fragrance oil into the pores of the aerogel. After that, 10 g of aerogel adsorbed with fragrance oil is added to 100 g of water, and then the oil droplets comprised in the pores in the aerogel are separated into the solvent using an overhead stirrer, and the remaining aerogel is filtered through a 0.45 um filter to manufacture an oil-water dispersion composition. After diluting water so that the weight ratio (W/W) of the oil droplets and water is 0.5:99.5, photographs were taken using a CryoTEM (JEOL company JEM-3011HR, FEI company Tecnai G2 spirit TWIN) device, and it is shown in FIG. 1. As a result of scaling as shown in the right photograph of FIG. 1, it was found that nano-scale oil droplets around 10 nm were dispersed.

Example 2

An oil-water dispersion composition was manufactured in the same manner as in Example 1, except for aerosil (Evonik company, product name R812S), whose pore size is 30 nm or less, instead of aerogel (JIOS company, product name AeroVa). The volume ratio (V/V) of the oil droplets and water was 0.5:99.5, and the obtained TEM photograph is shown in FIG. 2. As shown in FIG. 2, it was found that nano-scale oil droplets were dispersed.

Comparative Example 1

An oil-water dispersion composition was manufactured in the same manner as in Example 1, except that porous silica (ABC NANOTECH company, product name Silnos 190) having a pore size of 45 nm or more was used.

Comparative Example 2

After mixing fragrance oil and water in a volume ratio of 0.5:99.5, 5% surfactant (TCI company, Tween 60 product) was added thereto to manufacture an oil-water dispersion composition.

Manufacture of Non-Surfactant Type Water-Oil (W/O) Dispersion Composition

Example 3 of aerogel (JIOS company, product name AeroVa) having a pore size of 20 nm or less is heat-treated at 450° C. for 2 hours using a furnace (Furnace, JSR company, JSMF-45T). After adding 8 g of water to 4 g of heat-treated aerogel, an overhead stirrer (M TOPS® company, BL620D) is used to impregnate water into the pores of the aerogel. After that, g of aerogel adsorbed with water is added to 100 g of MCT (medium chain triglycerides) oil, and then the water droplets comprised in the pores in the aerogel are separated into the solvent using an overhead stirrer, and the remaining aerogel is filtered through a 0.45 um filter to manufacture an water-oil dispersion composition. The oil was diluted so that the weight ratio (W/W) of the water droplets and the oil was 2.5:97.5 to prepare a water-oil dispersion composition in which nano-scale water droplets were dispersed.

Example 4

A water-oil dispersion composition was manufactured in the same manner as in Example 1, except for aerosil (Evonik company, product name R812S), whose pore size is 30 nm or less, instead of aerogel (JIGS company, product name AeroVa). The volume ratio (V/V) of the water droplets and oil was 0.5:99.5.

Comparative Example 3

A water-oil dispersion composition was manufactured in the same manner as in Example 3, except that porous silica (ABC NANOTECH company, product name Silnos 190) having a pore size of 45 nm or more was used.

Comparative Example 4

After mixing water and oil in a volume ratio of 5% surfactant (TCI company, Span 60 product) was added thereto to manufacture a water-oil dispersion composition.

Experimental Example 1: Size Characteristics of Oil Droplets

After photographing the particle size of oil droplets or water in the oil-water dispersion compositions prepared in Examples 1 to 2 and Comparative Examples 1 to 2 and the water-oil dispersion compositions prepared in Examples 3 to 4 and Comparative Examples 3 to 4 using a CryoTEM (JEOL company JEM-3011HR, FEI company Tecnai G2 spirit TWIN) device, the average particle diameter of the droplets was measured and shown in Table 1.

TABLE 1

| | Average particle diameter of droplets (nm) |
|---|---|
| Example 1 | 10 |
| Example 2 | 19 |
| Comparative Example 1 | Measurement is not possible due to phase separation |
| Comparative Example 2 | Measurement is not possible due to phase separation |
| Example 3 | 12 |
| Example 4 | 18 |
| Comparative Example 3 | Measurement is not possible due to phase separation |
| Comparative Example 4 | Measurement is not possible due to phase separation |

Experimental Example 2: Transparency Characteristics

For the oil-water dispersion compositions prepared in Examples 1 to 2 and Comparative Examples 1 to 2 and the water-oil dispersion compositions prepared in Examples 3 to 4 and Comparative Examples 3 to 4, 3 mL of each dispersion composition was injected into the device without dilution, and scanned at UV 700-200 nm, and transparency at UV 650 nm was measured by using a UV-Vis Spectrometer (Thermo Scientific company Evolution 60S). The results are shown in Table 2 below.

TABLE 2

|  | 650 nm transparency |
| --- | --- |
| Example 1 | 100% |
| Example 2 | 100% |
| Comparative Example 1 | 55% |
| Comparative Example 2 | 96% |
| Example 3 | 100% |
| Example 4 | 100% |
| Comparative Example 3 | 43% |
| Comparative Example 4 | 92% |

As shown in Table 2, it was found that Examples 1 to 4 showed excellent transmittance, and Comparative Example 1 and Comparative Example 3 using porous silica having a pore size of 40 nm or more showed remarkably low transmittance.

Experimental Example 3: Phase Separation Characteristics

For the oil-water dispersion compositions prepared in Examples 1 to 2 and Comparative Examples 1 to 2 and the water-oil dispersion compositions prepared in Examples 3 to 4 and Comparative Examples 3 to 4, the phase separation characteristics were compared by centrifuging for 5 minutes at 13500 rpm using a centrifuge (WiseTis® company CF-10 Set).

As a result, it was confirmed that immediately after centrifugation, there is no significant difference from before centrifugation (FIG. 3), and as shown in FIG. 4, in the case of Comparative Example 1, Comparative Example 3, and Comparative Example 4 after 5 days, the composition is opaque or separation of the layers has occurred, and in the case of Examples 1 to 4, the phase of the compositions is stable.

Experimental Example 4: Temperature Stability Characteristics

For the oil-water dispersion compositions prepared in Examples 1 to 2 and Comparative Examples 1 to 2 and the water-oil dispersion compositions prepared in Examples 3 to 4 and Comparative Examples 3 to 4, changes in the appearance of the oil-water dispersion compositions prepared after 4 weeks of storage at 4° C., 30° C., and 45° C. were observed, and the results are shown in Table 3 and FIG. 5 (stored at 4° C. for 4 weeks), FIG. 6 (stored at 30° C. for 4 weeks), and FIG. 7 (stored at 45° C. for 4 weeks).

TABLE 3

| | Stability | | | | | | | | |
| --- | --- | --- | --- | --- | --- | --- | --- | --- | --- |
| | 4° C. | | | 30° C. | | | 45° C. | | |
| Item | 1 week | 2 weeks | 4 weeks | 1 week | 2 weeks | 4 weeks | 1 week | 2 weeks | 4 weeks |
| Example 1 | transparent | transparent | transparent | transparent | transparent | transparent | transparent | transparent | transparent |
| Example 2 | transparent | transparent | transparent | transparent | transparent | transparent | transparent | transparent | transparent |
| Comparative Example 1 | opaque | opaque | opaque | opaque | opaque | opaque | opaque | opaque | opaque |
| Comparative Example 2 | opaque | opaque | opaque | opaque | opaque | opaque | opaque | opaque | opaque |
| Example 3 | transparent | transparent | transparent | transparent | transparent | transparent | transparent | transparent | transparent |
| Example 4 | transparent | transparent | transparent | transparent | transparent | transparent | transparent | transparent | transparent |
| Comparative Example 3 | phase separation | phase separation | phase separation | phase separation | phase separation | phase separation | phase separation | phase separation | phase separation |
| Comparative Example 4 | opaque | opaque | opaque | opaque | opaque | opaque | opaque | opaque | opaque |

As a result, as shown in Table 3, it was found that Examples 1 to 4 are all transparent in appearance under the conditions of 4° C., 30° C., and 45° C., and thus showed good stability and Comparative Examples 1, 2, and 4 are all opaque in appearance under the conditions of 4° C., 30° C., and ° C., and in the case of Comparative Example 3, the stability is not maintained due to layer separation.

The invention claimed is:

1. A water-oil (W/O) dispersion composition consisting of polar solvent droplets and a non-polar solvent in which the polar solvent droplets are dispersed,
    wherein a transparency of the water-oil (W/O) dispersion composition is 90 to 100%,
    wherein the water-oil (W/O) dispersion composition does not comprise a surfactant,
    wherein the water-oil (W/O) dispersion composition does not comprise silica,
    wherein an average particle diameter of the polar solvent droplets is 20 nm or less,
    wherein the polar solvent droplets optionally comprise an active ingredient,
    wherein the polar solvent droplets are contained in an amount of 0.01 wt. % (W/W) to 30.0 wt. % (W/W) based on a total weight of the water-oil (W/O) dispersion composition,
    wherein polar solvent of the polar solvent droplets is water, and
    wherein the non-polar solvent is an oil, hexane, or a mixture thereof.

2. The water-oil (W/O) dispersion composition according to claim 1, wherein the active ingredient is one or more selected from the group consisting of adenosine, arbutin, vitamin C, vitamin B3, vitamin B5, vitamin H, acetylglucosamine, peptide, and derivatives thereof.

* * * * *